United States Patent [19]
Elam et al.

[11] Patent Number: 5,178,020
[45] Date of Patent: Jan. 12, 1993

[54] FIBER SAMPLER

[75] Inventors: Francis E. Elam, Dallas; David L. Adams, Carrollton, both of Tex.

[73] Assignee: Motion Control, Inc., Dallas, Tex.

[21] Appl. No.: 757,732

[22] Filed: Sep. 11, 1991

[51] Int. Cl.⁵ ............................................. G01N 1/04
[52] U.S. Cl. ............................................. 73/864.42
[58] Field of Search ...................... 73/863, 864, 864.41, 73/864.42

[56] References Cited

U.S. PATENT DOCUMENTS 3,057,019 10/1962 Hertel ............................... 73/863.41
4,391,153 7/1983 Taylor ............................... 73/864.41

Primary Examiner—Robert Raevis
Attorney, Agent, or Firm—Ross, Howison, Clapp & Korn

[57] ABSTRACT

A fiber sampler has a flat collection surface and a carriage movable toward the surface to press a mass of fiber placed on the surface. The carriage, which includes a foraminous plate parallel to the collection surface, is pressed against the fiber with a predetermined pressure kept constant from one sample to the next with the pressure applied, a rake composed of parallel needles spaced rearwardly from a deflection bar is passed across the top of the foraminous plate to extract sample fibers from the portion of fiber extending through the plate holes. At the end of rake travel, the fibers are held between a fixed stop plate on the carriage and a back plate movable with the needles. A pinch clamp assembly is provided which can be lowered to grip the fibers collected on the needles.

8 Claims, 3 Drawing Sheets

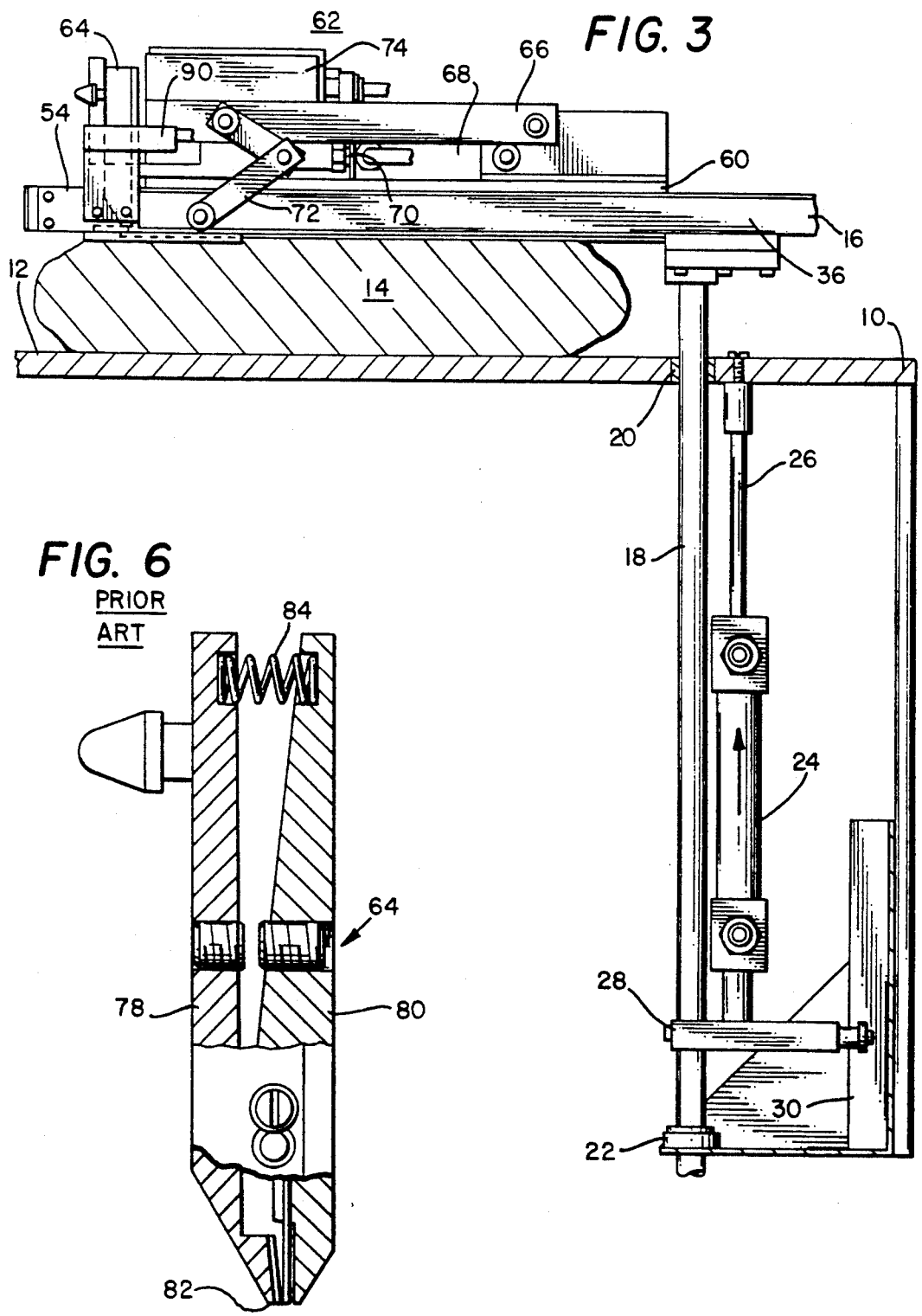

FIBER SAMPLER

TECHNICAL FIELD OF THE INVENTION

This invention relates to automated equipment for extracting a random sample of fibers from a mass of fibers for physical testing purposes.

BACKGROUND OF THE INVENTION

The testing of natural fibers for physical properties has been practiced in industry for many years. Examples of such testing are the measuring of average length and tensile strength of ginned cotton fibers. At the same time, samples are often optically tested for color and trash content. Typically, length and strength testing is carried out on a small sample of fibers extracted from a larger mass which is being analyzed.

One prior system for extracting and holding a small sample of cotton fibers is utilized in the fiber information equipment manufactured by the assignee of this application under the model designations "HVI 3000", "HVI 3500" and "HVI 4000." In such a system, a cylinder-operated, spring biased pinch clamp such as illustrated in FIG. 6 is lowered to the cotton mass. Then, the mechanical force provided by a pneumatic cylinder to maintain the clamp open is withdrawn, causing the spring-loaded clamp to shut, gripping a number of cotton fibers from the mass along the closure line of its jaws. In the HVI systems, the clamp is then used to hold the fibers throughout the remainder of their testing. The steps of combing and brushing are followed by length and strength testing on the fibers, all while held by the clamp. The system works very well, but it will be appreciated that the extracted fibers are taken from a very limited area of the cotton mass, since the pinch clamp operates essentially along a single short line. If the cotton mass exhibits a high degree of non-uniformity, this method of sampling may result in fibers which are not representative of the overall average characteristics of the entire mass from which they are extracted.

Another commercially used sampling system is depicted in U.S. Pat. No. 3,057,019 issued Oct. 9, 1962. In that system, a mass of cotton from which fiber samples are to be extracted is placed by the operator within a foraminous drum. The operator presses the cotton outwardly against the side wall of the drum, causing portions thereof to protrude outwardly through the holes in the drum surface. A rake is rotated around the outside of the drum to impale a sample of fibers on its teeth. This system does, because of its action, extract a sample from a broader physical area than that of the HVI devices discussed above. However, the system involves manual manipulation of the mass of cotton, and the manner in which the fibers are extracted is in part determined by the operator in pressing the cotton mass against the drum wall. As a result, periodic calibrations of the test equipment may be necessary because of inconsistent operator technique in producing the samples. Moreover, at such time as it becomes necessary to remove the fibers from the rake, the removal operation must be carried out manually.

Although the two prior art sampling systems discussed above are widely used in the industry, the advent of the present invention provides a sampling technique which produces representative samples even from a mass of cotton which is relatively heterogeneous. Moreover, the application of the present invention embodies a consistent and automatic sampling of the fibers for testing.

SUMMARY OF THE INVENTION

In accordance with the invention, a sampler is provided with a collection surface for receiving a mass of fibers such as a ginned cotton. A carriage having a foraminous plate parallel to the surface is movable toward and away from the collection surface. A rake is positioned on the side of the foraminous plate opposite the collection surface, and is movable parallel to the plate. There is provided a means for exerting constant pressure on the foraminous plate against the mass of fibers positioned on the collection surface so that portions of the fibers extend through the holes in the plate. Motive means causes sampling movement of the rake parallel to the plate while the means for exerting constant pressure is activated so that the rake collects random fibers from the mass protruding through the holes.

In the preferred form of the invention, the system also includes a pinch clamp which may be moved into position to engage fibers collected on the rake after the rake has completed its sampling movement, and to retain the fibers in the pinch clamp when the rake is returned to its starting position. In a particular form of the invention, the rake comprises an array of parallel needles having their points aligned and a deflector bar spaced forwardly from the pointed ends of the needles for depressing fibers extending through the foraminous plate as the rake travels across the plate. In the preferred embodiment of the invention, the collection surface and foraminous plate are planar so that the travel of the rake is linear.

BRIEF DESCRIPTION OF THE DRAWINGS

For a more complete understanding of the present invention and for further advantages thereof, reference is now made to the following Description of the Preferred Embodiments taken in conjunction with the accompanying Drawings in which:

FIG. 3 is a view similar to FIG. 1, with the carriage lowered for sampling;

FIG. 6 is a cross-sectional view of a prior art pinch clamp which is used in the sampler of FIGS. 1-5.

DESCRIPTION OF THE PREFERRED EMBODIMENTS

Figure 1:
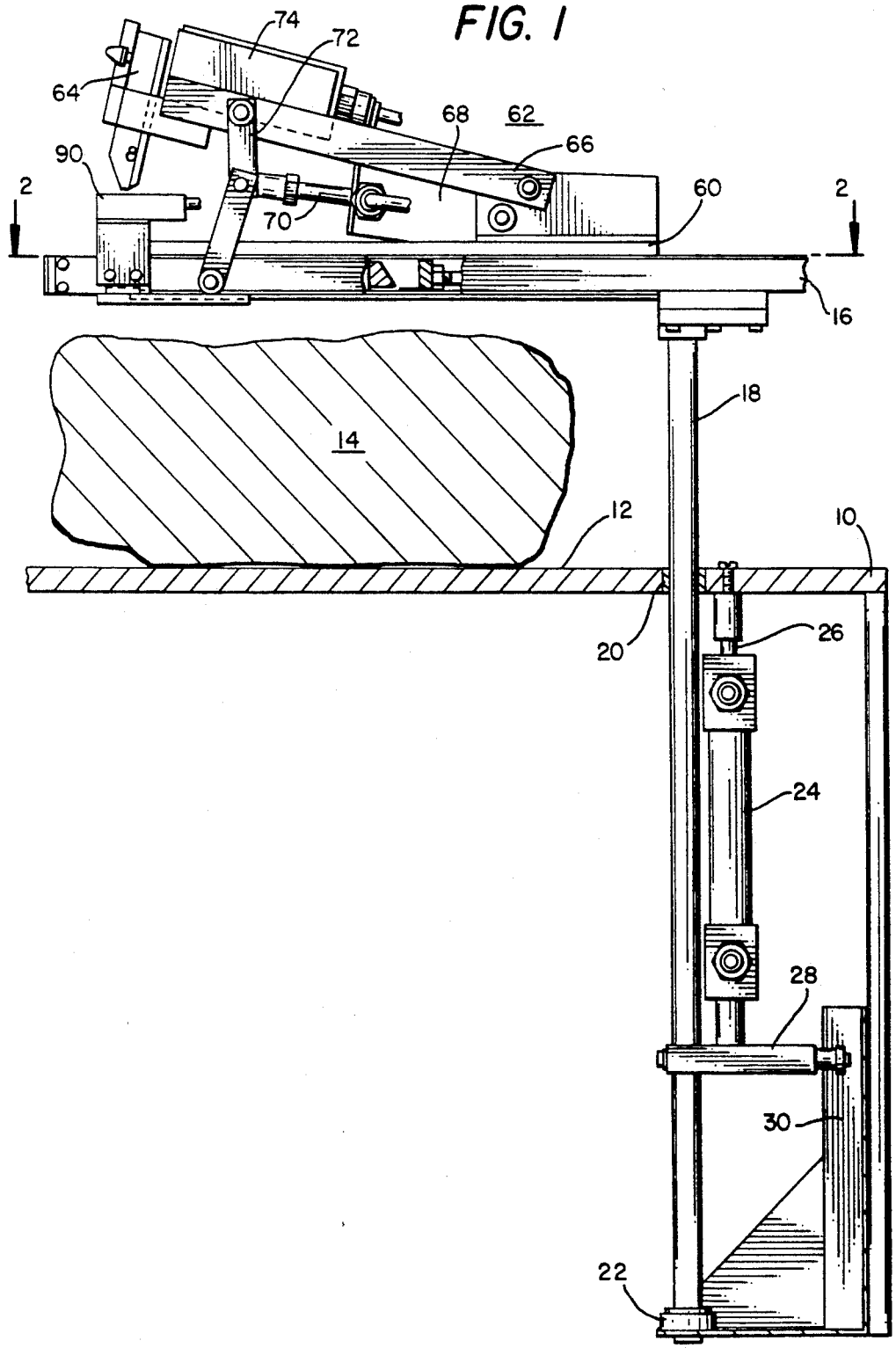
FIG. 1 is a side view, partially broken away, of a fiber sampler constructed in accordance with the invention, with its carriage raised and rake position withdrawn from the sampling area.

A fiber sampler constructed in accordance with the present invention is illustrated installed on a table 10 in FIG. 1. The flat horizontal surface 12 provided by the top of table 10 serves as a collection surface for receiving a mass of natural fiber 14 such as ginned cotton. Although not shown, a transparent window may be positioned in table 10 to receive the cotton mass, and optical detecting systems may be installed below the window for analyzing trash content and color of the cotton.

A carriage assembly 16 is positioned above the cotton 14, mounted on shaft 18, which extends downwardly through table 10 through aperture 20. Shaft 18 is mounted for reciprocating vertical movement, guided by guide member 22 at the lower end of the assembly. Motive power for the movement of the shaft 18, and thus of carriage 16, is provided by pneumatic cylinder 24 mounted below table 10. Cylinder 24 has its rod 26 connected to a platen 28 fixedly secured to shaft 18 near one end of the platen. The other end of platen 28 is guided in guide member 30. Cylinder 24 is controlled in its movement of lower shaft 18 and carriage 16 so that extension thereof is stopped at a preselected pressure in cylinder 24. This stop pressure is maintained at a constant level on each cotton sample, so that the pressure of carriage 16 on the cotton mass 14 is consistent from sample to sample.

Figure 2:
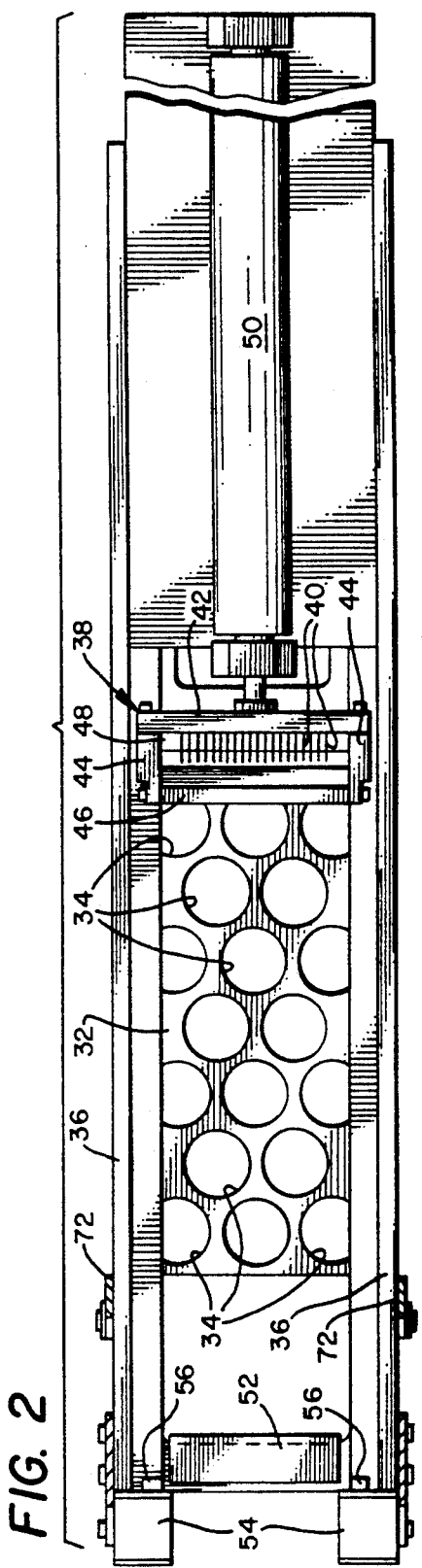
FIG. 2 is a top view of the carriage of the sampler of FIG. 1, with the pinch clamp mechanism removed.

As best seen in FIG. 2, a major portion of the floor of carriage 16 is formed by foraminous plate 32 which overlies the area of the cotton 14 placed on surface 12. Foraminous plate 32 has an array of apertures 34 through which portions of the cotton mass 14 will extend when the carriage 16 is pressed against the cotton with the predetermined pressure provided by cylinder 24. In the preferred embodiment constructed in accordance with this invention, plate 32 is approximately four by eight inches, and is provided with an array of 20 staggered apertures 34 which are approximately ⅞ of an inch in diameter.

Plate 32 extends between side rails 36 to form the floor of carriage 16 in the sampling area. A rake 38 is positioned above foraminous plate 32 between the side rails 36, and is shown in its retracted position in FIG. 2. Rake assembly 38 is formed by a parallel array of needles 40 mounted in needle bar 42. Side plates 44 are secured to each end of needle bar 42 to carry a deflector bar 46 having its lower surface aligned with the needles, and its trailing edge spaced slightly from the points of needles 40. A satisfactory spacing for the trailing edge of deflector bar 46 has been found to be approximately one-eighth of an inch. Rake assembly 38 is completed by back plate 48, which is secured to needle bar 42 and extends underneath needles 40 for a portion of their length. The area of rake 38 between the back plate 48 and deflector bar 46 is open so that cotton, after being depressed by passage of deflector bar 46, may extend upwardly through the open area to be engaged by needles 40. Needle bar 42 is connected to a rake activating cylinder 50, which may also be pneumatically driven.

The left end of carriage 16 as seen in FIG. 2 is provided with a stop plate 52 which is vertically aligned with back plate 48. End members 54 of carriage 16 carry spring loaded bumper pins 56 which are depressed by rake side plates 44 as the rake completes its sampling travel.

As best seen in FIG. 1, top rails 60 on carriage 16 mount a pinch clamp assembly 62 which may be operated to transfer samples collected by rake 38 to a pinch clamp such in FIG. 6, which has been used in the prior a In FIG. 1, the pinch clamp assembly is shown in its raised position. The pinch clamp 64 is removably carried at the end of a pivoting arm 66. A pneumatic cylinder 68 is provided for raising and lowering arm 66, and thus pinch clamp 64. The shaft 70 of cylinder 68 acts through two-bar linkage 72 to lower arm 66 and clamp 64 when the cylinder 68 retracts shaft 70. Arm 66 also carries clamp activating pneumatic cylinder 74 which, by its extension as in the prior art, forces the spring loaded clamp 64 to the open position so that its jaw may receive fibers.

As seen in FIG. 6, the prior art clamp 64 includes opposed members 78 and 80 to form a jaw 82 for gripping fibers. Springs 84 normally bias the clamp to the closed position. The force of cylinder 74 applied to the upper portion of member 80 overcomes the force of springs 84, moving the upper portions of members 78 and 80 together to cause jaw 82 to open to receive fiber. Removal of the opening force will cause the springs 84 to snap jaw 82 closed.

Although not illustrated in the drawings, an air nozzle may be positioned in the upper portion 90 of carriage 16 to blow directly along the jaw 82 of clamp 64 in its raised position, so that when a clamp is in position at the end of arm 66 the blast of air from the nozzle flows along the jaw.

The sequence of operation of the device provides a simple, automatic, and repeatable method of gathering a small fiber sample from a cotton mass placed on the collection surface 12. In the starting position illustrated in FIG. 1, cylinder 24 is retracted so that the carriage 16 is at the elevated position. The pinch clamp raising/lowering cylinder 68 is extended so that arm 66 is in the raised position illustrated. Pinch clamp opening cylinder 74 is retracted so that the pinch clamp is maintained in its normal closed position. Finally, rake activating cylinder 50 is retracted so that the rake is in the position illustrated in FIG. 2.

With the apparatus in this condition, the operator places the cotton mass 14 on collection surface 12 beneath carriage 16. A pinch clamp 64 is positioned on clamp arm 66, and the apparatus is activated. Blow away air through the nozzle mounted on member 90 is initially turned on and the pinch clamp cylinder 74 extended to open pinch clamp 64 so that any cotton specimen still retained in clamp 64 from a prior test is blown away into a vacuum collection system (not shown). Then the blow away air is turned off, and cylinder 24 is extended so that carriage 16 and plate 32 press down cotton sample 14 with a predetermined pressure. The rake cylinder 50 is activated to extend its rod causing the rake assembly to travel from right to left as seen in FIG. 2 so that cotton fibers are collected on needles 40 from the portions of mass 14 extending through apertures 34. As the deflector bar 46 passes, it depresses the cotton momentarily. The cotton then springs into the gap behind the deflector bar so that some of its fibers are caught on needles 40.

Figure 4:
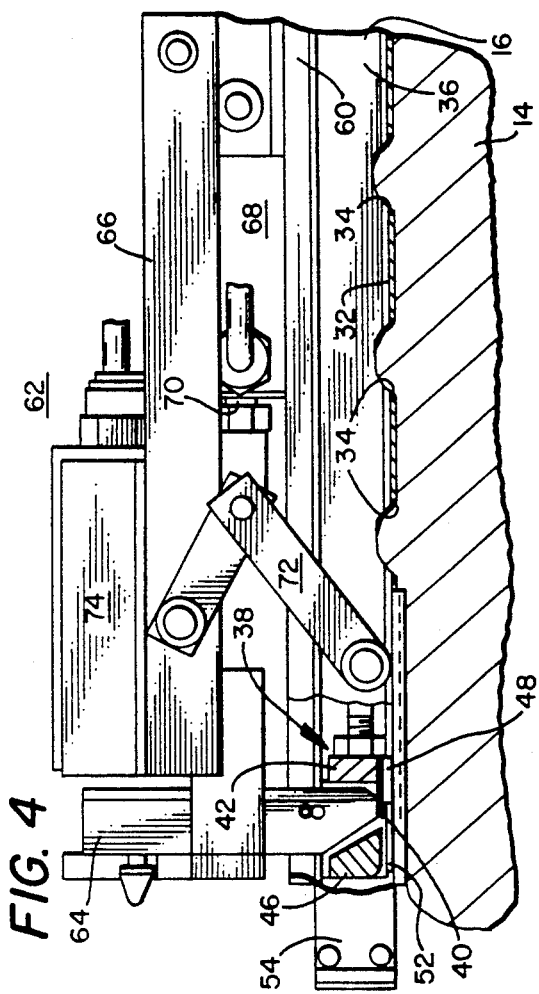
FIG. 4 is an enlarged broken-away view similar to FIG. 3, illustrating the rake at the end of its sampling travel, with the pinch clamp lowered.
Figure 5:
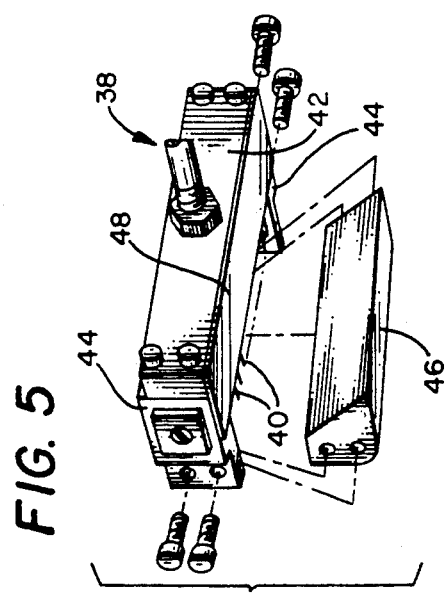
FIG. 5 is an exploded perspective view of the rake assembly.

As the rake assembly 38 reaches the end of the stroke, pins 56 are pushed rearwardly against their spring force, and back plate 48 abuts stop plate 52 to hold the collected fibers between plates 48 and 52. Cylinder 68 is retracted to lower clamp arm 66 and thus clamp 64 to the position shown in FIG. 4 so that the jaw 82 and clamp 64 is positioned directly over the needles at the juncture of back plate 48 and stop plate 52. The clamping cylinder 74 is then retracted to close clamp 64, securing the collected fibers in the jaw 82

At this point, the pressure in cylinder 50 is withdrawn, causing the pins 56 to push rake 38 backwardly to disengage needles 40 from the cotton fibers, which are now secured in clamp 64. All of the activating cylinders are then returned to their starting positions. At this point, the representative fiber sample is held in clamp 64, and may be subjected to further treatment and testing as in the prior art devices.

While the entire mechanism and operating sequence disclosed gives an efficient and automatic way of collecting fiber samples from a larger mass, it will be appreciated that advantages may be obtained from portions of the invention without using every element of the combination. For example, the rake assembly 38 in combination with the constant pressure downwardly on carriage 16 provides a repeatable way of collecting a small fiber sample on needles 40. If it is not desired to subject these representative fibers for testing through the mechanism of the pinch clamp 64 shown in FIG. 6, testing of the collected fibers may proceed in some other fashion.

In the disclosure of the invention described above, it will be appreciated that a reliably representative sample may be extracted from sequential batches of cotton subject to testing without violence to the repeatability of the test runs, and without repeated calibration of the equipment. The representative sample is drawn from a broad area of the cotton mass being analyzed in an automatic and repeatable manner because of the constant pressure of foraminous plate 32 on the cotton mass 14.

Whereas the present invention has been described with respect to specific embodiments thereof, it will be understood that various changes and modifications will be suggested to one skilled in the art and it is intended to encompass such changes and modifications as fall within the scope of the appended claims.

What is claimed is:

1. A fiber sampler comprising:
   (a) a collection surface for receiving a mass of fibers;
   (b) a carriage movable toward and away from the collection surface, including a foraminous plate parallel to the surface;
   (c) a reciprocatable rake position on the opposite side of the foraminous plate from the collection surface and movable parallel to the plate;
   (d) means for exerting constant pressure on the foraminous plate while the plate is engaging a mass of fibers positioned on the collection surface so that portions of the fibers extend through the holes in the foraminous plate; and
   (e) means for causing sampling movement of the rake parallel to the plate while the means for exerting constant pressure is activated, whereby the rake collects random fibers from the mass.

2. The sampler of claim 1, further comprising a pinch clamp activatable to grip fibers collected on the rake after the rake has completed its sampling movement, and to retain the fibers in the pinch clamp after the rake has returned to its starting position.

3. The sampler of claim 1, wherein the rake comprises an array of parallel needles with their points aligned.

4. The sampler of claim 3, further comprising a deflector bar movable with the rake and spaced forwardly from the points of the needles, for depressing the fibers extending through the foraminous plate as the rake travels across the plate.

5. The sampler of claim 3, further comprising a stop plate positioned on the carriage, and wherein the rake carries a back plate beneath the array of needles, so that the engagement of the back plate with the stop plate limits the sampling travel of the rake, whereby the extracted fibers are held between the back plate and the stop plate.

6. The sampler of claim 1, wherein the collection surface and foraminous plate are planar, and the rake travels in a straight line.

7. A cotton fiber sampler comprising:
   (a) a horizontal planar collection surface for receiving a mass of ginned cotton;
   (b) a carriage spaced from the collection surface and movable toward and away from the collection surface, the carriage comprising a flat foraminous plate parallel to the surface;
   (c) a rake movably mounted on the carriage and positioned on the opposite side of the foraminous plate from the collection surface, the rake mounted for movement traversing the plate, and comprising an array of parallel needles with points aligned and a deflector bar spaced from the needle points;
   (d) means for exerting constant pressure on the foraminous plate while the plate is engaging a mass of ginned cotton on the collection surface; and
   (e) means for causing sampling movement of the rake across the top of the foraminous plate to extract random fibers from the cotton mass.

8. The sampler of claim 7, further comprising a stop plate positioned on the carriage, and wherein the rake carries a back plate beneath the array of needles, so that the engagement of the back plate with the stop plate limits the sampling travel of the rake, whereby the extracted fibers are held between the back plate and the stop plate.

* * * * *